United States Patent
Yamanaka et al.

[11] 4,012,412
[45] Mar. 15, 1977

[54] 2,5-DI-SUBSTITUTED 4-OXAZOLEALKANOIC ACID AND ESTERS

[75] Inventors: Tsutomu Yamanaka; Toshihiro Kobayakawa, both of Fukuoka; Mitsuhiro Konishi, Oita; Kuniki Ikeda, Fukuoka, all of Japan

[73] Assignee: Yoshitomi Pharmaceutical Industries, Ltd., Osaka, Japan

[22] Filed: Mar. 12, 1975

[21] Appl. No.: 557,692

[30] Foreign Application Priority Data

Mar. 13, 1974 Japan .............................. 49-29548
Mar. 13, 1974 Japan .............................. 49-29549
Mar. 13, 1974 Japan .............................. 49-29550

[52] U.S. Cl. .......................... 260/307 R; 424/263; 424/272; 260/294.8 R; 260/295 R; 260/471 A
[51] Int. Cl.² ....................................... C07D 263/42
[58] Field of Search ................................ 260/307 R

[56] References Cited
UNITED STATES PATENTS 3,413,297  11/1968  Miki et al. ....................... 260/307 R
3,565,909  2/1971   Miki et al. ....................... 260/307 R

FOREIGN PATENTS OR APPLICATIONS 46-43383  12/1971  Japan ............................. 260/307 R

*Primary Examiner*—Donald G. Daus
*Assistant Examiner*—David E. Wheeler
*Attorney, Agent, or Firm*—Sughrue, Rothwell, Mion, Zinn & Macpeak

[57] ABSTRACT

2,5-Di-substituted 4-oxazolealkanoic acids and esters thereof of the formula:

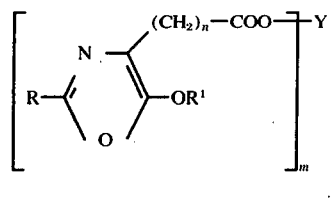

wherein $m$ represents an integer of 1 to 2; $R^1$ represents an alkyl group having 1 to 4 carbon atoms; $n$ represents an integer of 1 to 2; R represents a mono- or di-substituted phenyl group (in which the substituents are selected from the group consisting of a halogen atom, a methyl group, a methoxy group, a nitro group, a trifluoromethyl group, a phenyl group, a halogen-substituted phenyl group, a phenoxy group and a halogen-substituted phenoxy group), a pyridyl group, a halogen-substituted pyridyl group, a furyl group, a halogen-substituted furyl group, a thienyl group, a halogen-substituted thienyl group, a naphthyl group or a halogen-substituted naphthyl group; when $m$ represents an integer of 1, Y represents an hydrogen atom, an alkyl group having 1 to 2 carbon atoms, a benzyl group or a pyridylmethyl group; and when $m$ represents an integer of 2, Y represents a trimethylene group. These compounds are useful as drugs for the treatment of arteriosclerosis, thrombosis and hypertension with lipid metabolism disorder.

6 Claims, No Drawings

2,5-DI-SUBSTITUTED 4-OXAZOLEALKANOIC ACID AND ESTERS

This invention relates to novel and therapeutically valuable compounds of the formula:

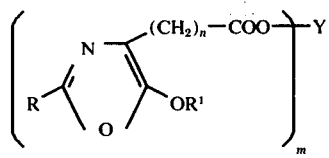

wherein $m$ represents an integer of 1 to 2; $R^1$ represents an alkyl group having 1 to 4 carbon atoms, $n$ represents an integer of 1 to 2; R represents a mono- or di-substituted phenyl group (in which the substituents are selected from the group consisting of a halogen atom, a methyl group, a methoxy group, a nitro group, a trifluoromethyl group, a phenyl group, a halogen-substituted phenyl group, a phenoxy group and a halogen-substituted phenoxy group), a pyridyl group, a halogen-substituted pyridyl group, a furyl group, a halogen-substituted furyl group, a thienyl group, a halogen-substituted thienyl group, a naphthyl group or a halogen-substituted naphthyl group; when $m$ represents an integer of 1, Y represents an hydrogen atom, an alkyl group having 1 to 2 carbon atoms, a benzyl group or a pyridylmethyl group (e.g. 2-pyridylmethyl, 3-pyridylmethyl); and when $m$ represents an integer of 2, Y represents a trimethylene group.

The compounds of formula (I) can be produced by one of the following methods (a) to (c).

a. In the case of compounds of formula [I] wherein $m$ represents an integer of 1 and Y represents an alkyl group having 1 to 2 carbon atoms, a benzyl group or a pyridylmethyl group:

i. By dehydrating a compound of the formula:

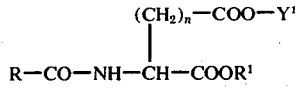

wherein $Y^1$ represents an alkyl group having 1 to 2 carbon atoms, a benzyl group or a pyridylmethyl group and other symbols are as defined above.

The dehydration is carried out by treating the compound of formula [II] with a dehydrating agent (e.g. phosphorus pentoxide, phosphorus pentachloride, thionyl chloride, phosphorus oxychloride, tosyl chloride) in an inert solvent (e.g. benzene, toluene, ligroin, chloroform, 1,2-dichloromethane, methylene chloride, carbon tetrachloride), preferably with phosphorus pentoxide in refluxing 1,2-dichloroethane in the presence of diatomaceous earth or glass beads as promoter of stirring.

ii. By reacting a compound of the formula:

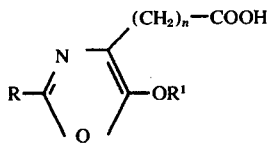

wherein R, $R^1$ and $n$ are as defined above, or a functional derivative thereof with a compound of the formula:

$$X - Y^1 \quad [IV]$$

wherein X represents a halogen atom, an alkyl- or arylsulfonyloxy group (e.g. p-tolylsulfonyloxy or methylsulfonyloxy) or hydroxy group and $Y^1$ is as defined above.

The functional derivative of the compound of formula [III] is, for example, acid halide, acid anhydride or mixed acid anhydride.

The reaction is usually carried out in an aprotic polar solvent (e.g. dimethylformamide, dimethylacetamide, dimethylsulfoxide) in the presence of an organic base (e.g. triethylamine, pyridine), or in a water or a mixture of water and water-miscible organic solvent in the presence of an inorganic base (e.g. sodium hydroxide, sodium carbonate, sodium bicarbonate), or under heating in an alcohol corresponding to the compound of formula [IV] in the presence of a catalyst (e.g. hydrochloric, sulfuric acid).

In the case of the reaction of the functional derivative of the compound of formula [III] with the compound of formula [IV], the reaction is usually carried out in an alcohol corresponding to the compound of formula [IV] in the presence of an organic base (e.g. triethylamine, pyridine) at appropriate temperature depending on the reactivities of the starting compounds.

b. In the case of compounds of formula [I] wherein $m$ represents an integer of 1 and Y represents a hydrogen atom, by hydrolyzing a compound of the formula:

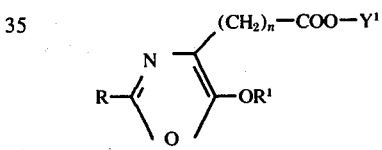

wherein $Y^1$, R, $R^1$ and $n$ are as defined above.

The hydrolysis is carried out by treating the compound of formula [V] with an acid or an alkali, preferably with an alkali hydroxide (e.g. NaOH, KOH), in a solvent such as an alcohol (e.g. methanol, ethanol), a ketone (e.g. acetone, methyl ethyl ketone), an ether (e.g. dioxane, tetrahydrofuran), water or a mixture thereof at room temperature.

c. In the case of compounds of formula [I] wherein $m$ represents an integer of 2, by reacting a compound of formula [III] or a functional derivative thereof with a compound of the formula:

$$X - (CH_2)_3 - X \quad [VI]$$

wherein X is as defined above.

The reaction is carried out in a manner as described in (ii) above.

The compounds of formula [I] possess excellent pharmacological properties such as hypolipidemic and anti-thrombotic actions, as shown, for example, by the following tests, and are useful as drugs for the treatment of arteriosclerosis, thrombosis and hypertension with lipid metabolism disorder.

For example, the compounds of formula [I] listed below have the following pharmacological properties:
A: ethyl 2-p-chlorophenyl-5-ethoxy-4-oxazoleacetate B: 3-pyridylmethyl 2-p-chlorophenyl-5-ethoxy-4-oxazoleacetate C: ethyl 2-(3,4-dichlorophenyl)-5-ethoxy-4-oxazoleacetate D: 3-[2-(4-pyridyl)-5-ethoxy-4-oxazole]propionic acid The tests were carried out by the following methods:

Hypolipidemic Action i. Male rats with normal serum lipid (Table 1)

Table 1 shows the change in serum lipid levels observed after the 5 days consecutive administration of the test compound to Wistar strain male rats weighing 150 – 200 g. Each test group was composed of more than 5 rats. The test compound was orally given by a gastric tube. Serum cholesterol and triglyceride levels were measured by the standard methods using an autoanalyzer (Technicon Inc.). The levels in the control (placebo) group were considered at 100% and the reduction (%) in the test group was calculated.

ii. Dietary hyperlipidemia in male mice (Table 2)

dd-Strain male mice weighing 20 – 25 g. were used. Each group was composed of 8 mice. Animals were fed with NMF food (Oriental Yeast Co., Tokyo) containing 1% of cholesterol, 0.2% of cholic acid and 5% of olive oil, and the serum cholesterol level was measured by the use of an autoanalyzer after 5 days administration of the test compound. The levels in the test group was compared with that in the control group given the same diet.

iii. Triton hyperlipidemia in male mice (Table 3)

Each group was composed of eight dd-strain male mice weighing 20 – 25 g. Immediately after intraperitoneal administration of the test compound to the animals, Triton WR-1339 was intraveniously given. Eighteen hours after Triton administration, the serum cholesterol level was measured and compared with that of the control group treated in the same way.

Anti-thrombotic Action

One hour after oral administration of the test compound to male mice weighing 20 – 25 g., the tail vein was punctured and the end of bleeding time was measured in Ringer's solution of 37° C according to the method described by Karl Dottl in "Medizin und Chemie", 3, 276 (1936). The bleeding time induced by platelet thrombi was compared with that of the control group, and the rate of prolongation was calculated as an index of anti-thrombotic activity. The results are shown in Table 4.

Acute Toxicity

The test compound was orally administered to groups each of 5 male mice and rats respectively. The $LD_{50}$ was calculated from the lethal rate (50%) within two days after administration of the test compound. The results are shown in Table 5.

Table 1

| Compound | Dose (mg/kg/day) | Lowering Rate (%) of Serum Cholesterol Level | Lowering Rate (%) of Serum Triglyceride Level |
|---|---|---|---|
| A | 100 | 25 | 45 |
| B | 100 | 22 | 41 |
| Clofibrate (for comparison) | 100 | 31 | 35 |

Table 2

| Compound | Dose (mg/kg/day) | Lowering Rate (%) of Serum Cholesterol Level |
|---|---|---|
| A | 100 | 41 |
|  | 50 | 21 |
| B | 100 | 43 |
| Clofibrate (for comparison) | 100 | 16 |
|  | 50 | 0 |

Table 3

| Compound | Dose (mg/kg/day) | Lowering Rate (%) of Serum Cholesterol Level |
|---|---|---|
| A | 100 | 32 |
|  | 50 | 26 |
| C | 100 | 35 |
|  | 25 | 18 |
| Clofibrate (for comparison) | 100 | 10 |

Table 4

| Compound | Dose (mg/kg/day) | Prolongation Rate (%) of the Bleeding Time |
|---|---|---|
| D | 100 | 439 |
|  | 50 | 321 |
|  | 25 | 209 |
|  | 12.5 | 107 |
| Acetylsalicylic Acid (for comparison) | 50 | 268 |
|  | 25 | 65 |
|  | 12.5 | 22 |
| Clofibrate (for comparison) | 100 | 38 |

Table 5

| Compound | $LD_{50}$ (mg/kg) per os Mouse | $LD_{50}$ (mg/kg) per os Rat |
|---|---|---|
| A | 4000 | >4000 |
| B | >4000 | >4000 |
| C | 2000 | >4000 |
| D | >2000 | >2000 |
| Clofibrate (for comparison) | 1500 | 2300 |

In view of the tests including those mentioned above, the compounds [I] of the present invention can be administered safely as drugs for the treatment of arteriosclerosis, thrombosis and hypertension with lipid metabolism disorder, in the form of a pharmaceutical preparation with a suitable and conventional carrier or adjuvant, administered orally, without harm to the patient.

The oral daily dose of compound A for human adults usually ranges from 150 to 600 milligrams.

Formulation Example 50 mg. Tablets are prepared from the following compositions:

| Compound A | 50 mg. |
| Lactose | 90 mg. |
| Starch | 19 mg. |

| -continued | |
| --- | --- |
| Formulation Example | |
| Microcrystalline Cellulose | 15 mg. |
| Talc | 5 mg. |
| Magnesium Stearate | 1 mg. |
| | 180 mg. |

The present invention will be better understood from the following examples, which are merely intended to be illustrative and not limitative of the present invention.

EXAMPLE 1

A suspension of 30 g. of diethyl N-p-chlorobenzoyl-L-aspartate in 120 ml. of 1,2-dichloroethane is added with stirring and heating under reflux to a suspension of 26 g. of phosphorus pentoxide and 16 g. of diatomaceous earth in 200 ml. of 1,2-dichloroethane. The mixture is heated under reflux with stirring for 30 minutes. The reaction mixture is cooled and made alkaline with a saturated aqueous solution bicarbonate solution, and the diatomaceous earth is filtered off. The filtrate is allowed to separate into an aqueous layer and an organic layer in a separatory funnel. The aqueous layer is extracted with a small amount of ethyl acetate. The extract and the organic layer are combined and the combined solution is washed with water and concentrated. The residue is recrystallized from hexane to give 17.8 g. of ethyl 2-p-chlorophenyl-5-ethoxy-4-oxazoleacetate melting at 80° – 82° C.

EXAMPLE 2

A solution of 10.5 g. of diethyl N-p-methoxybenzoyl-L-aspartate in 30 ml. of 1,2-dichloroethane is added with stirring and heating under reflux to a suspension of 10 g. of phosphorus pentoxide and 5.4 g. of diatomaceous earth in 55 ml. of 1,2-dichloroethane. The reaction mixture is treated in an identical manner as described in Example 1 to give 9.4 g. of a concentrated residue. The residue is recrystallized from hexane to give 7.1 g. of ethyl 2-p-methoxyphenyl-5-ethoxy-4-oxazoleacetate as white needles melting at 48 – 49° C.

EXAMPLE 3

A solution of 60 g. of diethyl N-3,4-dichlorobenzoyl-L-aspartate in 300 ml. of 1,2-dichloroethane is gradually added dropwise with stirring and heating under reflux to a suspension of 90 g. of phosphorus pentoxide and 60 g. of diatomaceous earth in 550 ml. of 1,2-dichloroethane. After the addition, the mixture is heated under reflux with stirring for about 1 hour. The reaction mixture is cooled and made alkaline with an aqueous sodium bicarbonate solution cooled with ice added. The diatomaceous earth is filtered off and the filtrate is transferred into s separatory funnel. The lower 1,2-dichloroethane layer is dried over sodium sulfate and concentrated in vacuo. The residue is recrystallized from a mixture of hexane and ethanol to give 31 g. of ethyl 2-(3,4-dichlorophenyl)-5-ethoxy-4-oxazoleacetate as white fine crystalline powder melting at 77°–78° C.

EXAMPLE 4

Diethyl N-m-trifluoromethylbenzoyl-L-asparate (20 g.) is treated with 21 g. of phosphorus pentoxide and 11 g. of diatomaceous earth in an identical manner as described in Example 3. The crude product is recrystallized from hexane to give 7.5 g. of ethyl 2-m-trifluoromethylphenyl-5-ethoxy-4-oxazoleacetate melting at 41° – 43° C.

EXAMPLE 5

A solution of 10.4 g. of potassium hydroxide in 100 ml. of 80% methanol is added dropwise with stirring at room temperature to a solution of 50 g. of ethyl 2-p-chlorophenyl-5-ethoxy-4-oxazoleacetate (produced by the procedure of Example 1) in 200 ml. of methanol. The mixture is stirred at room temperature for 3 hours, and the methanol is distilled off in vacuo. The residue is diluted with water and extracted with ether. The aqueous layer is cooled with ice and adjusted to pH 3.5 with hydrochloric acid. The resulting crystals are collected by filtration, dried and recrystallized from ethyl acetate to give 31.0 g. of 2-p-chlorophenyl-5-ethoxy-4-oxazoleacetic acid as white scales melting at 144° – 146° C.

EXAMPLE 6

A solution of 4.8 g. of potassium hydroxide in 35 ml. of 80% methanol is added dropwise with stirring at room temperature to a solution of 17.5 g. of ethyl 2-p-methoxyphenyl-5-ethoxy-4-oxazoleacetate (produced by the procedure of Example 2) in 15 ml. of 80% methanol. The reaction mixture is treated in an identical manner as described in Example 5. The crude product is recrystallized from ethyl acetate to give 11.3 g. of 2-p-methoxyphenyl-5-ethoxy-4-oxazoleacetic acid melting at 129° – 131° C.

EXAMPLE 7

A solution of 8.5 g. of potassium hydroxide in 90 ml. of 80% methanol is added dropwise with stirring at room temperature to a solution of 40 g. of ethyl 2-(3,4-dichlorophenyl)-5-ethoxy-4-oxazoleacetate (produced by the procedure of Example 3) in 400 ml. of methanol. The mixture is stirred at room temperature for a period of from 3 to 4 hours, and the methanol is distilled off in vacuo. The residue is diluted with water and extracted with ether. The aqueous layer is cooled with ice and adjusted to pH about 3 with dilute sulfuric acid. The precipitated crystals are collected by filtration, dried and recrystallized from ethanol to give 25 g. of 2-(3,4-dichlorophenyl)-5-ethoxy-4-oxazoleacetic acid as white crystals melting at 165° –167° C.

EXAMPLE 8

A solution of 15.0 g. of ethyl 2-m-trifluoromethylphenyl-5-ethoxy-4-oxazoleacetate (produced by the procedure of Example 4) in 15 ml. of methanol is treated with a solution of 2.9 g. of potassium hydroxide in 30 ml. of 80% methanol in an identical manner as described in Example 7. The crude product is recrystallized from a mixture of hexane and ethanol to give 4.5 g. of 2-m-trifluoromethylphenyl-5-ethoxy-4-oxazoleacetic acid melting at 134° – 135° C.

EXAMPLE 9

To a solution of 20 g. of 2-p-chlorophenyl-5-ethoxy-4-oxazoleacetic acid in 100 ml. of dimethylformamide are added 60 ml. of triethylamine and 40 ml. of ethyl bromide, and the mixture is stirred overnight at room temperature. The course of the reaction is followed by thin-layer chromatography. When the starting compounds disappear, 1 liter of water is added to the reaction mixture, and the mixture is extracted with ethyl acetate. The organic layer is washed with water, with dilute hydrochloric acid and further with water, and then dried and concentrated. The residue is recrystallized from hexane to give 19.0 g. of ethyl 2-p-chlorophenyl-5-ethoxy-4-oxazoleacetate melting at 84° – 85° C.

EXAMPLE 10

To a solution of 4.0 g. of 2-p-chlorophenyl-5-ethoxy-oxazoleacetic acid in 60 ml. of methanol is added 0.1 ml. of concentrated sulfuric acid, and the mixture is heated for about 30 minutes. After cooling, triethylamine is added to the reaction mixture, and the methanol is distilled off in vacuo. Water and ethyl acetate are added to the residue, and the mixture is shaken. The organic layer is washed with water, dried over sodium sulfate and concentrated. The residue is recrystallized from hexane to give 3.5 g. of methyl 2-p-chlorophenyl-5-ethoxy-4-oxazoleacetate melting at 63° – 65° C.

EXAMPLE 11

To a solution of 1.0 of 2-p-chlorophenyl-5-ethoxy-4-oxazoleacetic acid in 15 ml. of benzene is added 1.0 ml. of thionyl chloride, and the mixture is heated for 2 hours. The benzene is distilled off in vacuo, and the residue is dissolved in 2 ml. of ether. Methanol (4 ml.) is added with cooling with ice to the solution followed by addition of 1.0 ml. of triethylamine, and the mixture is allowed to stand overnight. The solvent is distilled off in vacuo. The residue is purified and recrystallized in a similar manner as Example 10 to give 0.6 g. of methyl 2-p-chlorophenyl-5-ethoxy-4-oxazoleacetate melting at 63° – 65° C.

EXAMPLE 12

To a solution of 6.0 g. of 2-p-chlorophenyl-5-ethoxy-4oxazoleacetic acid in 15 ml. of dimethylformamide and 6.5 ml. of triethylamine is added 2.3 g. of 1,3-dibromopropane, and the mixture is stirred at a temperature of from 35° to 40° C for 13 hours. Water is added to the mixture. The precipitated crystals are collected by filtration, dried and recrystallized from a mixture of ethyl acetate and ethanol to give 4.5 g. of trimethylene bis(2-p-chlorophenyl-5-ethoxy-4-oxazoleacetate) melting at 129° – 131° C.

EXAMPLE 13 to 64

Using the procedures set forth in the above examples, but substituting equivalent amount of the appropriate starting materials, the following compounds are also produced:

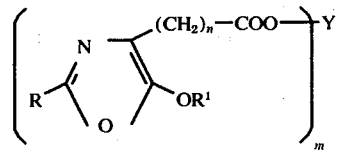

| Example | R | R¹ | Y | m | n | Physical Constant |
|---|---|---|---|---|---|---|
| 13 | o-chlorophenyl | ethyl | ethyl | 1 | 1 | $n_D^{20}$ = 1.5502 |
| 14 | m-chlorophenyl | ethyl | ethyl | 1 | 1 | M.P. 44–45° C |
| 15 | p-chlorophenyl | butyl | ethyl | 1 | 1 | $n_D^{20}$ = 1.5422 |
| 16 | p-chlorophenyl | ethyl | ethyl | 1 | 2 | M.P. 48–50° C |
| 17 | p-chlorophenyl | ethyl | benzyl | 1 | 1 | M.P. 66–68° C |
| 18 | p-nitrophenyl | ethyl | ethyl | 1 | 1 | M.P. 93–94° C |
| 19 | 4-(p-chlorophenyl)phenyl | ethyl | ethyl | 1 | 1 | M.P. 88–90° C |
| 20 | 3-fluoro-4-chlorophenyl | ethyl | ethyl | 1 | 1 | M.P. 71–72° C |
| 21 | 3-methyl-4-chlorophenyl | ethyl | ethyl | 1 | 1 | M.P. 52–54° C |
| 22 | 2-fluoro-4-chlorophenyl | ethyl | ethyl | 1 | 1 | M.P. 86–88° C |
| 23 | 2-furyl | ethyl | ethyl | 1 | 1 | $n_D^{20}$ = 1.5228 |
| 24 | 2-thienyl | ethyl | ethyl | 1 | 1 | $n_D^{20}$ = 1.5537 |
| 25 | 5-chloro-2-thienyl | ethyl | ethyl | 1 | 1 | $n_D^{20}$ = 1.5595 |
| 26 | β-naphthyl | ethyl | ethyl | 1 | 1 | M.P. 72–74° C |
| 27 | 4-chloro-1-naphthyl | ethyl | ethyl | 1 | 1 | M.P. 83–85° C |
| 28 | p-chlorophenyl | ethyl | 3-pyridyl-methyl | 1 | 1 | M.P. 85–85° C |
| 29 | p-chlorophenyl | butyl | 3-pyridyl-methyl | 1 | 1 | M.P. 65–66° C |
| 30 | p-chlorophenyl | ethyl | 2-pyridyl-methyl | 1 | 1 | M.P. 67–68° C |
| 31 | p-nitrophenyl | ethyl | 2-pyridyl-methyl | 1 | 1 | M.P. 101–103° C |
| 32 | 2-furyl | ethyl | 3-pyridyl-methyl | 1 | 1 | $n_D^{20}$ = 1.5405 |
| 33 | 5-chloro-2-thienyl | ethyl | 3-pyridyl-methyl | 1 | 1 | M.P. 71–73° C |
| 34 | 4-chloro-1-naphthyl | ethyl | 3-pyridyl-methyl | 1 | 1 | M.P. 98–100° C |
| 35 | 6-chloro-3-pyridyl | ethyl | 3-pyridyl-methyl | 1 | 1 | M.P. 96–97° C |
| 36 | p-chlorophenyl | ethyl | H | 1 | 2 | M.P. 129–131° C |
| 37 | m-chlorophenyl | ethyl | H | 1 | 1 | M.P. 133–134° C |
| 38 | p-chlorophenyl | methyl | H | 1 | 1 | M.P. 120–122° C |
| 39 | p-chlorophenyl | butyl | H | 1 | 1 | M.P. 138–140° C |
| 40 | p-tolyl | ethyl | H | 1 | 1 | M.P. 119–121° C |
| 41 | p-nitrophenyl | ethyl | H | 1 | 1 | M.P. 188.5–189.5° C |
| 42 | 4-(p-chlorophenyl)phenyl | ethyl | H | 1 | 1 | M.P. 141–143° C |
| 43 | 4-(p-chlorophenoxy)phenyl | ethyl | H | 1 | 1 | M.P. 138–140° C |
| 44 | 2,4-dichlorophenyl | ethyl | H | 1 | 1 | M.P. 119–120° C |
| 45 | 3-fluoro-4-chlorophenyl | ethyl | H | 1 | 1 | M.P. 158–160° C |
| 46 | 2-fluoro-4-chlorophenyl | ethyl | H | 1 | 1 | M.P. 131–133° C |
| 47 | 3-methyl-4-chlorophenyl | ethyl | H | 1 | 1 | M.P. 141–143° C |
| 48 | 2-furyl | ethyl | H | 1 | 1 | M.P. 109–110° C |
| 49 | 5-bromo-2-furyl | ethyl | H | 1 | 1 | M.P. 131–132° C |

-continued

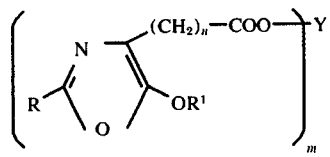

| Example | R | R¹ | Y | m | n | Physical Constant |
|---|---|---|---|---|---|---|
| 50 | 2-thienyl | ethyl | H | 1 | 1 | M.P. 129–130° C |
| 51 | 5-chloro-2-thienyl | ethyl | H | 1 | 1 | M.P. 140–141° C |
| 52 | β-naphthyl | ethyl | H | 1 | 1 | M.P. 158–160° C |
| 53 | α-naphthyl | ethyl | H | 1 | 1 | M.P. 124–126° C |
| 54 | 4-chloro-1-naphthyl | ethyl | H | 1 | 1 | M.P. 159–160° C |
| 55 | 3-pyridyl | ethyl | H | 1 | 1 | M.P. 166–168° C |
| 56 | 3-pyridyl | ethyl | H | 1 | 2 | M.P. 121–123° C |
| 57 | 4-pyridyl | ethyl | H | 1 | 2 | M.P. 146–147° C |
| 58 | 2-pyridyl | ethyl | H | 1 | 2 | M.P. 143–145° C |
| 59 | 2-pyridyl | ethyl | H | 1 | 1 | M.P. 145–147° C |
| 60 | 4-pyridyl | ethyl | H | 1 | 1 | M.P. 180–181° C |
| 61 | 6-chloro-3-pyridyl | ethyl | H | 1 | 1 | M.P. 164–165° C |
| 62 | 2-chloro-3-pyridyl | ethyl | H | 1 | 2 | M.P. 115–117° C |
| 63 | 2-chloro-3-pyridyl | ethyl | H | 1 | 1 | M.P. 151–153° C |
| 64 | 6-chloro-3-pyridyl | ethyl | H | 1 | 2 | M.P. 122–124° C |

What is claimed is:

1. A compound of the formula:

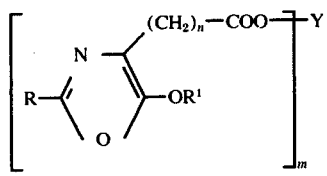

wherein $m$ represents an integer of 1 to 2; $R^1$ represents an alkyl group having 1 to 4 carbon atoms; $n$ represents an integer of 1 to 2; R represents a mono- or di-substituted phenyl group (in which the substituents are selected from the group consisting of a halogen atom, a methyl group, a methoxy group, a nitro group, a trifluoromethyl group, a phenyl group, a halogen-substituted phenyl group, a phenoxy group and a halogen-substituted phenoxy group), a furyl group, a halogen-substituted furyl group, a thienyl group or, a halogen-substituted thienyl group, when $m$ represents an integer of 1, Y represents an hydrogen atom, an alkyl group having 1 to 2 carbon atoms, or a benzyl group; and when $m$ represents an integer of 2, Y represents a trimethylene group.

2. A compound of the formula:

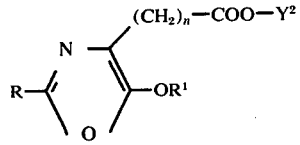

wherein $R^1$ represents an alkyl group having 1 to 4 carbon atoms; $n$ represents an integer of 1 to 2; R represents a mono- or di-substituted phenyl group (in which the substituents are selected from the group consisting of a halogen atom, a methyl group, a methoxy group, a nitro group, a trifluoromethyl group, a phenyl group, a halogen-substituted phenyl group, a phenoxy group and a halogen-substituted phenoxy group), a furyl group, a halogen-substituted furyl group, a thienyl group or a halogen-substituted thienyl group, and $Y^2$ represents an hydrogen atom, an alkyl group having 1 to 2 carbon atoms, or a benzyl group.

3. A compound of the formula:

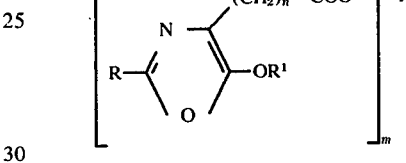

wherein $m$ represents an integer of 1 to 2; $R^1$ represents an alkyl group having 1 to 4 carbon atoms; $n$ represents an integer of 1 to 2; R represents a mono- or di-substituted phenyl group (in which the substituents are selected from the group consisting of a halogen atom, a methyl group, a methoxy group, a nitro group, a trifluoromethyl group, a halogen-substituted phenyl group and a halogen-substituted phenoxy group), a halogen-substituted furyl group, a thienyl group or a halogen-substituted thienyl group; when $m$ represents an integer of 1, Y represents a hydrogen atom, an alkyl group having 1 to 2 carbon atoms or a benzyl group; and when $m$ represents an integer of 2, Y represents a trimethylene group.

4. A compound of the formula:

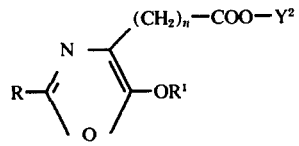

wherein $R^1$ represents an alkyl group having 1 to 4 carbon atoms; $n$ represents an integer of 1 to 2; R represents a mono- or di-substituted phenyl group; (in which the substituents are selected from the group consisting of a halogen atom, a methyl group, a methoxy group, a nitro group, a trifluoromethyl group, a halogen-substituted phenyl group and a halogen-substituted phenoxy group), a halogen-substituted furyl group, a thienyl group or a halogen-substituted thienyl group; and $Y^2$ represents a hydrogen atom, an alkyl group having 1 to 2 carbon atoms or a benzyl group.

5. A compound of the claim 1:
ethyl 2-p-chlorophenyl-5-ethoxy-4-oxazoleacetate.

6. A compound of the claim 1:
ethyl 2-(3,4-dichlorophenyl)-5-ethoxy-4-oxazoleacetate.

* * * * *